US00PP10201P

United States Patent [19]

Marriott

[11] Patent Number: Plant 10,201

[45] Date of Patent: Jan. 20, 1998

[54] SCAVEOLA PLANT NAMED 'BLUE FANDANGO'

[75] Inventor: Neil R. Marriott, Stawell, Australia

[73] Assignee: Koala Blooms Pty. Ltd., Mordialloc, Australia

[21] Appl. No.: 693,979

[22] Filed: Aug. 8, 1996

[30] Foreign Application Priority Data

May 30, 1994 [AU] Australia ..... 94/118

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,929 8/1992 Rother ..... Plt./68.1

OTHER PUBLICATIONS

Upovrom Disk 1997/01 Search Report 1997.

*Primary Examiner*—Howard J. Locker
*Assistant Examiner*—Kent L. Bell
*Attorney, Agent, or Firm*—C. A. Whealy

[57] ABSTRACT

A distinctive cultivar of Scaevola plant named 'Blue Fandango', characterized by its mounded upright plant habit; rapid growth rate; relatively large flowers; and bright purple petals with yellow-green base.

2 Drawing Sheets

The present invention relates to a new and distinct cultivar of Scaevola plant, botanically known as *Scaevola aemula*, and named 'Blue Fandango'. It is anticipated that the plant of this application will be marketed under the name "Outback Royal Fan".

The new cultivar originated from a cross made by the inventor of unidentified selections of the species *Scaevola aemula*. The cultivar 'Blue Fandango' was discovered and selected by the inventor as a flowering plant within the progeny of the stated cross in a controlled environment in Deep Lead, Victoria, Australia.

Subsequent asexual reproduction of the new cultivar by terminal cuttings taken at Deep Lead, Victoria, Australia, has shown that the unique features of this new Scaevola are stable and reproduced true to type in successive generations of asexual reproduction.

The following traits have been repeatedly observed and are determined to be the unique characteristics of 'Blue Fandango'. These characteristics in combination distinguish the new Scaevola as a new and distinct cultivar:

1. Mounded upright plant habit that is suitable for hanging basket containers.
2. Rapid growth rate.
3. Relatively large flowers.
4. Bright purple petals with yellow-green base. Plants of the new Scaevola are similar in petal color to plants of the *Scaevola aemula* cultivar 'Purple Fan'. In side-by-side comparisons conducted in a controlled environment in Deep Lead, Victoria, Australia, plants of the new Scaevola were more upright in growth habit, taller, and had a slightly paler purple petal color. A detailed comparison of the differences between plants of the cultivar 'Purple Fan' and the cultivar 'Blue Fandango' appears in Chart A at the end of the specification.

The new Scaevola has not been observed under all possible environmental conditions. The phenotype may vary significantly with variations in environment such as temperature, light level and daylength, without, however, any variance in genotype.

The accompanying colored photographs illustrate the overall appearance and flower color of the new Scaevola, showing the colors as true as it is reasonably possible to obtain in colored reproductions of this type.

The first photograph comprises a top perspective view of a typical plant of the new Scaevola.

The second photograph comprises a closer view of typical flowers of the new Scaevola.

The flower color in these photographs may appear different from the actual flower color due to light reflectance.

The following observations, measurements, values, and comparisons describe plants grown in Deep Lead, Victoria, Australia, under outdoor conditions with day temperatures ranging from 15° to 30° C., night temperatures ranging from 10° to 25° C., and light levels ranging from 5,000 to 9,000 footcandles. Color references are made to The Royal Horticultural Society Colour Chart except where general terms of ordinary dictionary significance are used.

Classification:

*Botanical.*—*Scaevola aemula* cultivar 'Blue Fandango'.

*Commercial.*—Scaevola.

Parentage:

*Male or pollen parent.*—Unidentified selection of *Scaevola aemula*.

*Female or seed parent.*—Unidentified selection of *Scaevola aemula*.

Propagation:

*Type.*—By cuttings.

*Time to initiate and develop roots.*—7 to 20 days at temperatures of 20° C.

*Rooting habit.*—Numerous, fibrous, and freely branching.

Plant description:

*General appearance.*—Mounded, upright herbaceous plant, suitable for hanging basket containers. Lateral stems may be upright or semi-upright. Appropriate for 15-cm to 25-cm hanging basket containers. To produce a 15-cm finished flowering plant from rooted cuttings, 16 to 20 weeks are required depending on temperature and light level.

*Plant height.*—35 to 45 cm from soil level to top of plant plane.

*Branching.*—Moderate branching, typically 2 to 4 lateral branches develop when the terminal apex is removed (pinched). Lateral branches are typically 20 to 30 cm in length.

*Growth rate.*—Rapid.

*Vigor.*—Moderate.

*Foliage description.*—Arrangement: Alternate, single. Quantity: 8 to 25 per lateral branch. Leaf shape: Spatulate. Leaf apex: Obtuse. Leaf base: Attenuate.

Leaf margin: Serrated. Leaf aspect: Flat. Leaf length: 2.5 to 5.5 cm. Leaf width: 1.5 to 2.5 cm. Leaf texture: Leathery, slightly rough, and slightly pubescent. Leaf attachment: Sessile. Leaf color: Young leaves: Abaxial surface: 143A. Adaxial surface: 143A. Fully expanded leaves: Adaxial surface: 146B. Abaxial surface: 146C. Venation: Adaxial surface: Inconspicuous. Abaxial surface: 145B.

Flower description:

*Flower type and shape.*—Semi-circular, fan-shaped flowers with five petals fused at the base to form a tubular flower throat. Flower throat open along the upper side exposing reproductive organs. Flowers last on the plant for 2 to 3 weeks and for about 1 week as a fresh cut flower. Flowers self-cleaning.

*Flower arrangement.*—Flowers arise from leaf axils with one flower per axil. Flowers sessile.

*Natural flowering season.*—Natural flowering season is late spring to fall. Plants flower continuously during this period.

*Quantity of flowers.*—6 to 12 per lateral stem.

*Flower diameter.*—2.5 to 3 cm.

*Fragrance.*—None.

*Petals.*—Shape: Obovate. Apex: Mucronate. Margin: Entire. Length: About 1.5 cm. Width: 4 to 6 min. Color: When opening: 87B. Adaxial surface: 87A with yellow-green, 154D, base. With subsequent development, color fades to 87C, then to 87D and eventually to 98B with base, 153D. Abaxial surface: 87B to 87C.

*Flower bud.*—Length: About 1.5 mm. Diameter: 2 to 4 mm. Color: 145B.

*Sepals.*—Quantity: Five. Shape: Broadly triangular. Apex: Pointed. Margin: Ciliate. Texture: Smooth. Color: 144C.

*Reproductive organs.*—Stamens: Quantity: Five to six. Anther shape: Elongated. Anther size: About 1.5 mm. Anther color: 161A. Pistils: Quantity: One. Stigma shape: Bilobate. Stigma color: 83B and 11D. Style length: About 1.2 cm.

Disease resistance: No resistance or susceptibility to diseases observed.

Seed production: Seed production is typically not observed.

CHART A

| CHARACTERISTIC | 'BLUE FANDANGO' | 'PURPLE FAN' |
|---|---|---|
| PLANT SHAPE | Mounded | Procumbent |
| GROWTH HABIT | Upright | Spreading |
| PLANT HEIGHT | 35 to 45 cm | 10 to 20 cm |
| LEAF COLOR, YOUNG LEAVES, ABAXIAL SURFACE | 143A | 147A |
| LEAF COLOR, YOUNG LEAVES, ADAXIAL SURFACE | 143A | 147B |
| LEAF COLOR, MATURE LEAVES, ABAXIAL SURFACE | 146B | 137B |
| LEAF COLOR, MATURE LEAVES, ADAXIAL SURFACE | 146C | 146A |
| LEAF MARGIN | Serrated | Coarsely serrated |
| PETAL LENGTH | About 1.5 cm | About 1.1 cm |
| PETAL COLOR, OPENING | 87B | 88A |
| PETAL COLOR, MATURE ABAXIAL SURFACE | 87A with yellow-green, 154D, base | 88B with yellow-green, 151A, base |
| PETAL COLOR, MATURE ADAXIAL SURFACE | 87B to 87C | 88B |

It is claimed:

1. A new and distinct Scaevola plant named 'Blue Fandango', as illustrated and described.

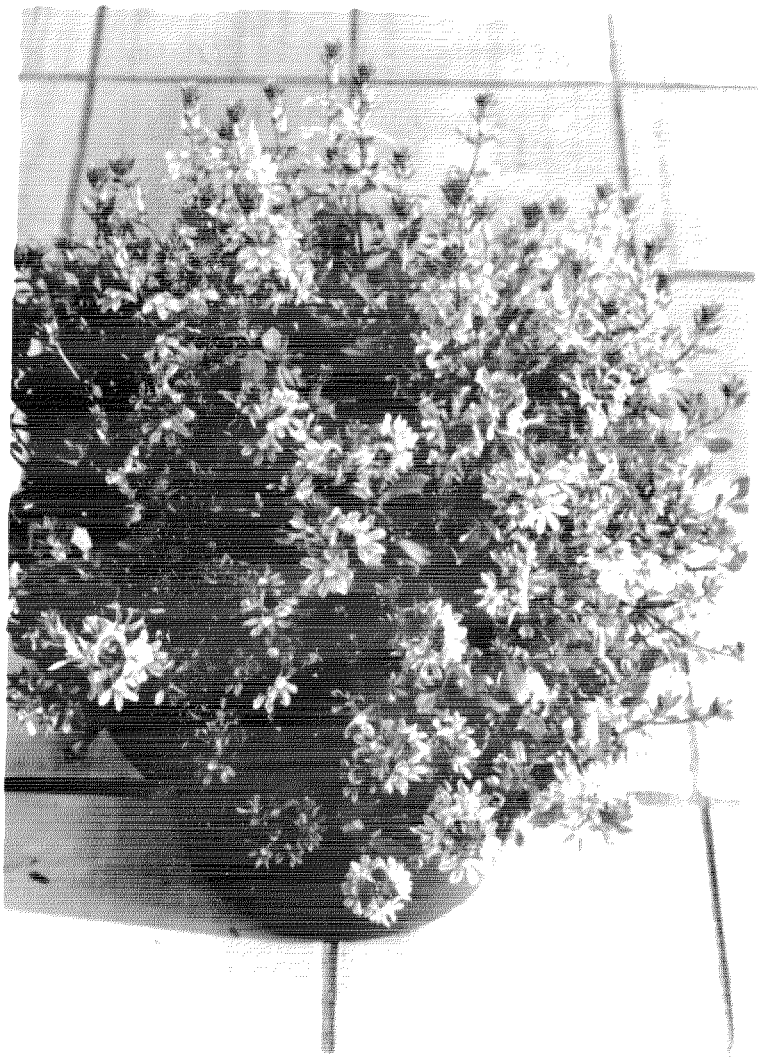

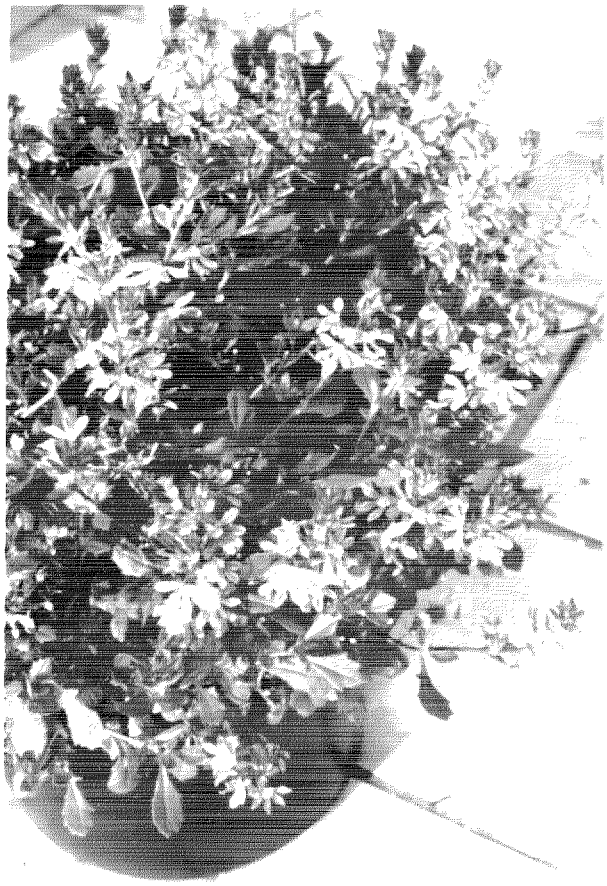

* * * * *